United States Patent
Hartunian

[11] Patent Number: 6,058,517
[45] Date of Patent: May 9, 2000

[54] SPORTS NECK BRACE

[76] Inventor: Byron V. Hartunian, 4 Saw Mill Brook Way, Woburn, Mass. 01801

[21] Appl. No.: 09/239,483

[22] Filed: Jan. 28, 1999

[51] Int. Cl.$^7$ ...................................................... A61F 5/00
[52] U.S. Cl. .................................................. 2/468; 602/18
[58] Field of Search ................................. 2/455, 468, 44, 2/45; 602/17, 18

[56] References Cited

U.S. PATENT DOCUMENTS

| Re. 35,290 | 7/1996 | Druskoczi | 602/18 |
|---|---|---|---|
| 2,806,471 | 9/1957 | Breese | 128/87 |
| 3,024,784 | 3/1962 | Monfardini | 128/75 |
| 3,189,917 | 6/1965 | Sims . | |
| 3,320,950 | 5/1967 | McElvenny | 128/75 |
| 3,497,872 | 3/1970 | Mitchell . | |
| 3,855,631 | 12/1974 | Ettinger . | |
| 3,964,474 | 6/1976 | Fox | 128/87 B |
| 4,425,667 | 1/1984 | Harrison . | |
| 4,501,023 | 2/1985 | Bilberry . | |
| 4,590,622 | 5/1986 | Wolfe . | |
| 4,996,720 | 3/1991 | Fair . | |
| 5,275,581 | 1/1994 | Bender | 602/18 |
| 5,404,590 | 4/1995 | Monica, Jr. | 2/468 |

Primary Examiner—Gloria M. Hale
Assistant Examiner—Tejash Patel
Attorney, Agent, or Firm—John P. McGonagle

[57] ABSTRACT

A sports neck brace for use by players in a contact team sport. The brace is made from foam and is adapted to being fastened about a wearer's neck thereby surrounding the wearer's neck with 360° of cushioning. The brace is self-contained and has a generally inverted frustum shape with the portion contacting a wearer's helmet being angled generally upward and outward from the bottom of a wearer's helmet.

5 Claims, 5 Drawing Sheets

SPORTS NECK BRACE

BACKGROUND OF THE INVENTION

This invention relates to protective athletic equipment, and in particular, to a neck guard and protector for reducing or eliminating neck injuries.

Body contact team sports such as football, hockey and lacrosse have progressed to a high degree of sophistication in recent years. With this progress, protective equipment has been developed for protecting many areas of the body, especially the head. Football helmets in particular have been developed to the point where they are sometimes used as a weapon, as well as for protection. Neck injuries, however, continue to plague contact sports players. There are various reasons for this.

As forces during a contact sports game are applied to a player's helmet from any and all directions, the neck is subjected to a variety of stresses including axial compression, flexion, extension, lateral bending, torsion and/or a combination of these. Axial compression stress will be defined as force exerted along the head's vertical axis, a force applied downward on the top of the head and through to the neck. Flexion stress will be defined as a forward and downward force exerted on the head, pushing the chin toward the chest. Extension stress will be defined as an upward force exerted on the chin causing a backward tilt of the head. Lateral bending stress will be defined as force exerted on the side of the head causing side-to-side tilting of the head. Torsion stress will be defined as a rotational force applied along the vertical axis of the neck.

When these forces are excessive or when a lack of training and conditioning of the player is present, injuries to the neck frequently result such as strained muscles, sprained ligaments and tendons as well as more serious damage to vertebrae, discs and nerves. These injuries, which on occasion can be fatal, manifest themselves in other forms both permanent and otherwise such as paralysis, headaches, neuritis, neuralgia, constant or intermittent pain, nausea, fainting, weakness, neck stiffness and the like. Compounding this problem are the newer plastic helmets which utilize suspended webbing and foam padding and are sometimes used as battering rams in the process of running, blocking and tackling, in a game becoming more intense and aggressive. Further aggravating the problem is the fact that players are becoming bigger and faster, thereby increasing the force of "hits" on opposing players. The present-day comfortable and efficient helmets serve to give players a feeling of security, which results in an increasing use of the head to force extra yards from a run or apply additional leverage in a block or tackle.

Neck injuries in body contact team sports result when the head is exposed to impact forces as described above, and the cervical vertebrae, discs, muscles, ligaments and/or tendons are damaged, sometimes permanently affecting the spinal cord and nerves. Blows are delivered to a player's helmeted head from all directions during a game, and among the most dangerous of these blows is the impact which causes extreme tension and compression in the cervical region. The application of force to the head of a player without neck protection is transferred directly to the player's neck, often causing injuries to the supporting structures previously listed.

One of the most commonly used neck protective devices is a sponge neck collar, i.e., "roll" collar. The roll collar normally comprises a horseshoe-shaped roll of sponge rubber which is worn around the rear and sides of a player's neck. The roll collar serves as a stop-gap between the player's head and shoulders to prevent lateral bending as well as extension and may give some protection against axial compression. In this manner, injuries due to extreme backward or lateral bending of the head to either side may be reduced.

However, the conventional sponge roll collar has serious limitations. One of the most dangerous situations for a player arises when the head is forced forward and downward by impact, i.e., flexion. This places a substantial and dangerous amount of posterior tension and frontal compression on the cervical vertebrae and discs. The roll collar does not prevent or reduce neck injuries caused when a player's head is violently rammed forward and downward into his chest, as often happens in a football game during a head-on tackle or pile-up. Nor does the roll collar protect well against direct blows to the frontal area of the neck. Moreover, because a properly fitted collar prevents extension and rotation movement beyond a predetermined position, it is often difficult or impossible for a player such as a lineman to wear a roll collar and still be able to get his head back or turned to the side to see his opponent.

Various modifications to the conventional roll collar have been made in the prior art in an attempt to overcome its basic limitations, including flattening of the roll collar's top surface. However, an even more significant problem with the conventional roll collar and the various prior art hybrids, is caused by the contact between the collar's top surface and the bottom edge portion of a wearer's helmet. Any frontal (upward), axial or lateral force will cause the helmet to cantilever about the top surface of a roll collar, regardless of whether the top surface is flat or rounded. Since the modern helmet is extremely rigid and snugly fitted about the wearer's head, the wearer's head will also cantilever. The cantilevering effect can exaggerate the forces applied to the neck, thereby exerting potentially excessive cervical tension and compression, resulting in serious injury. Because some roll collars are attached to the shoulder pads, hits to the shoulder pads can cause a reverse effect, i.e., force translated to the neck.

U.S. Pat. No. 4,996,720 to J. D. Fair attempts to solve the prior art roll collar cantilevering problem by providing a protective vest having a resilient upstanding collar. Although the collar portion of the Fair invention addresses the cantilevering problem it ignores the problem of a player's head being forced forward and downward by impact, i.e., it ignores axial compression and flexion blows to the head. There is even less axial support than the traditional roll collar. The Fair collar is also restrictive in that it is fixedly attached to the vest. This serves, not to dissipate the energy from a blow to the wearer's head, but to transfer that energy to other portions of the wearer's anatomy. Furthermore, the collar provides a whiplash counter effect when frontal forces are exerted to the wearer's face causing rapid extension of the head.

SUMMARY OF THE INVENTION

The present invention addresses the problem of prior art protective neck devices by providing a sports neck brace which overcomes the limitations of prior art roll collars. The present invention neck brace is made from foam and is adapted to being fastened about a wearer's neck thereby surrounding the wearer's neck with 360° of cushioning. The brace has a generally inverted frustum shape with the portion contacting the wearer's helmet angled generally upward and outward from the bottom of a wearer's helmet.

This "captured" position minimizes the possibility of the helmet/head cantilevering when in contact with the brace. In fact the brace provides cushioned, counter pressure regardless of direction, i.e., to extension, flexion, lateral and axial forces. The brace is self-contained and not fastened to the shoulder pads, helmet or any vests. By not being attached to the shoulder pads, forces on the pads are not readily transferred to the neck or head. It also permits a player complete freedom of movement in rotating his head while still having his neck fully protected. The brace meets the requirements that the head and neck be substantially unrestrained to permit adequate range of unrestricted motion in order for an athlete to effectively participate in team contact sports.

The bottom of the brace is shaped with a resulting contour which, in an uncompressed state, reduces the coefficient of friction between the neck brace and shoulder pads. However, with compression, the brace bottom digs into the shoulder pads thereby reducing rotation somewhat like a screw hole mechanism. This provides additional stability and a counter-rotational effect to harmful torque forces on the helmet.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF INVENTION

Figure 1:
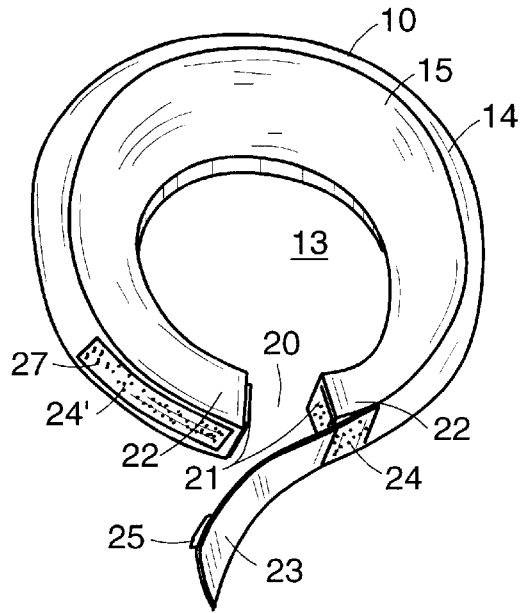
FIG. 1 is a perspective view of a sports neck brace.
Figure 2:
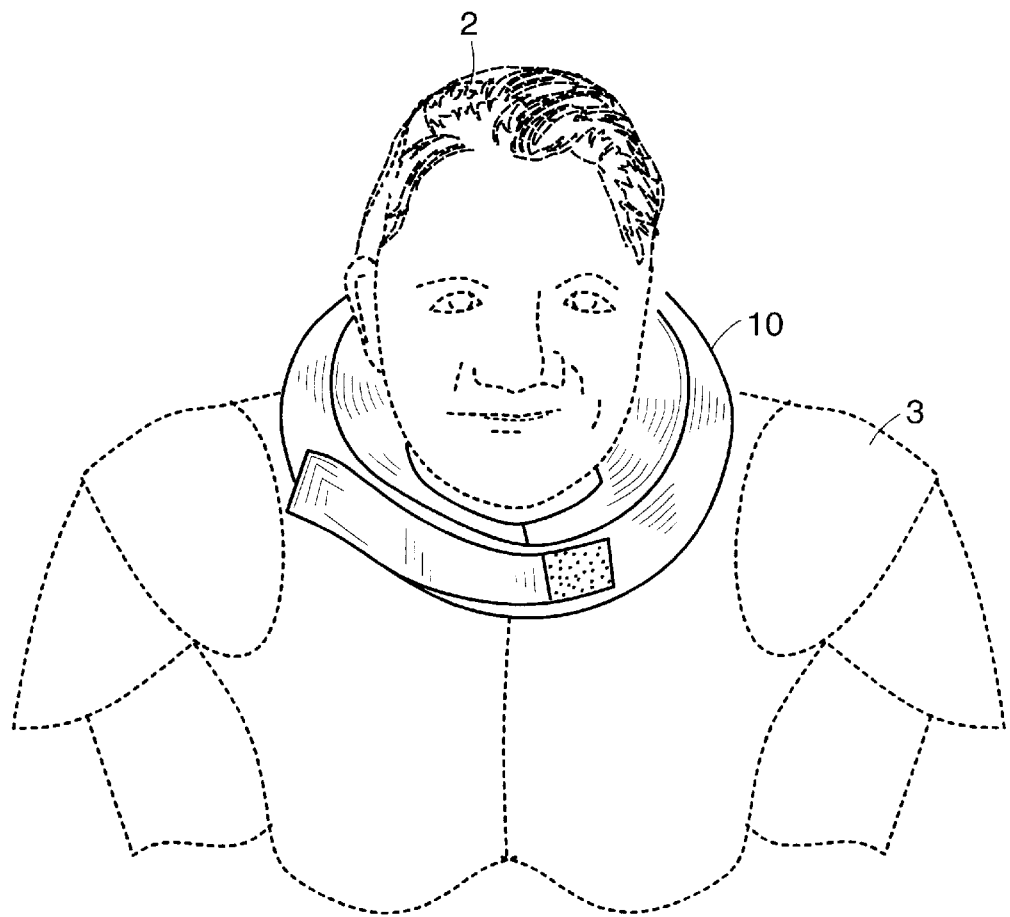
FIG. 2 is a perspective view of the sports neck brace of FIG. 1 shown being worn.
Figure 3:
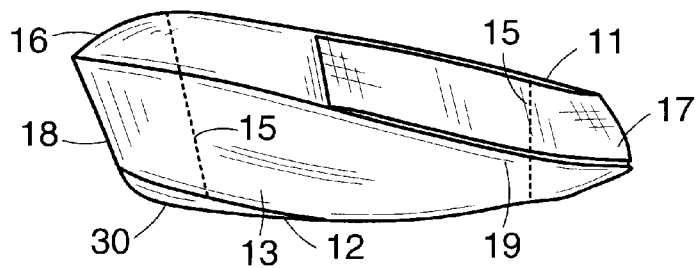
FIG. 3 is a side elevational view of the neck brace.
Figure 4:
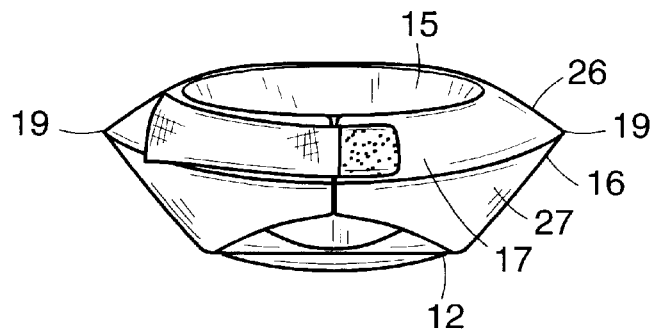
FIG. 4 is a front elevational view of the neck brace.
Figure 5:
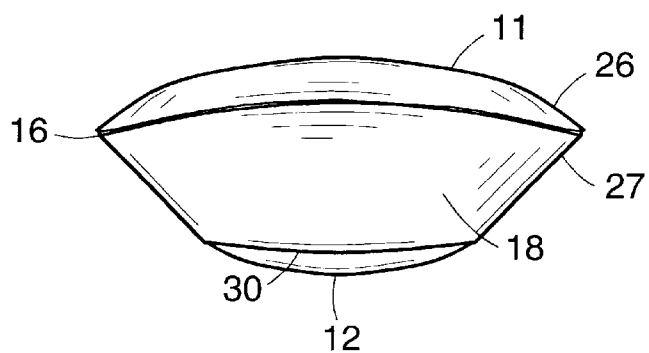
FIG. 5 is a rear elevational view of the neck brace.
Figure 6:
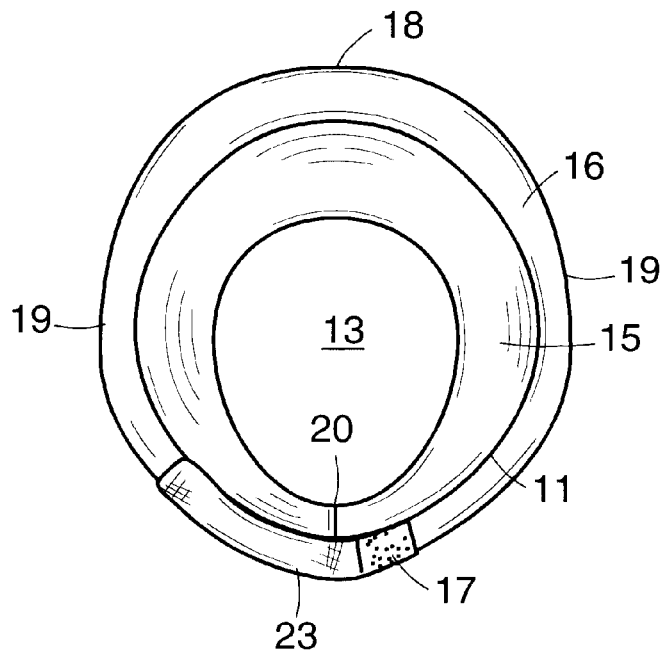
FIG. 6 is a top view of the neck brace.
Figure 7:
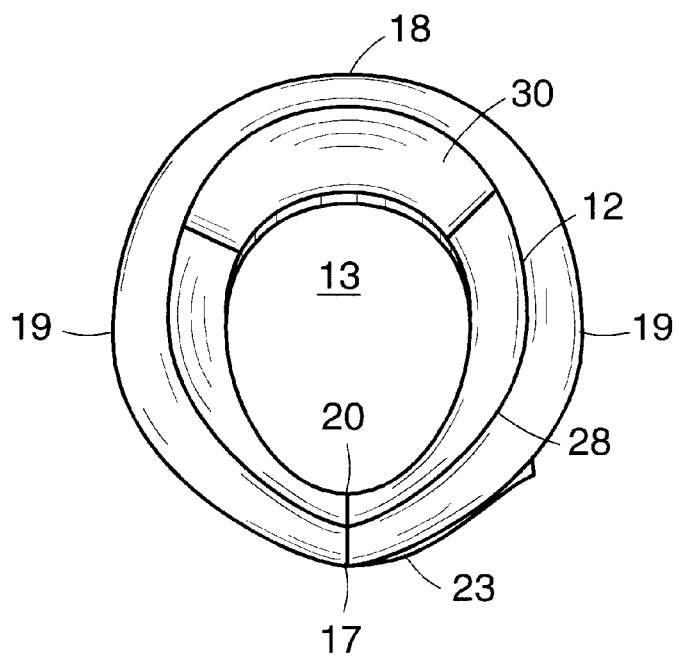
FIG. 7 is a bottom view of the neck brace.

Referring to the drawings in detail wherein like elements are indicated by like numerals, there is shown an embodiment of the invention presented as a sports neck brace 10. The brace 10 is worn about a user's neck at the top neck opening of a user's shoulder pads 3. The brace 10 has a top 11, bottom 12, and a wall 14 extending from the bottom 12 to the top 11 and defining a generally inverted frustum-shaped central opening 13. The wall 14 has an interior surface 15 and exterior surface 16. The brace 10 has a front 17, rear 18, and two sides 19. The front 17 has a vertical opening 20 adapted to being closed by means of hook and pile fasteners 21, sold under the VELCRO trademark, fasteners 21 attached to wall ends 22. A strap 23 is fixedly attached to the front 17 of one of the wall end portions 24. The strap 23 has a VELCRO fastener 25 attached to its inside surface 26. The opposite front wall end portion 24' has a VELCRO fastener 27 attached thereto adapted to being joined with the strap VELCRO fastener 25.

The wall exterior surface 16 has an upper portion 26 and lower portion 27. The upper portion 26 slants downwardly and radially outwardly from the top 11 of the central opening 13 and terminating in the lower portion 27. The lower portion 27 slants downwardly and radially inwardly from the upper portion 26 and terminates at the bottom 12 of the central opening 13.

The bottom 12 is contoured forming a radial ridge 28. The ridge 28 provides reduced friction in the brace's uncompressed state thereby allowing a player's head 2 substantial freedom of movement prior to contact. However, with compression from contact, the brace bottom 12 digs into the shoulder pads 3 thereby reducing rotation and protecting the neck.

In an alternate embodiment, a wedge-shaped cut-out portion 30 is removably attached to the brace bottom 12 at the brace rear 18. Removing the wedge 30 permits even greater neck extension for players in a down stance position.

The brace 10 is preferably made from foam, such as resilient closed-cell polyethylene, covered by a smooth, plasticized material, such as vinyl. However, any resilient material or substance may be used, such as rubber or gel.

Figure 8:
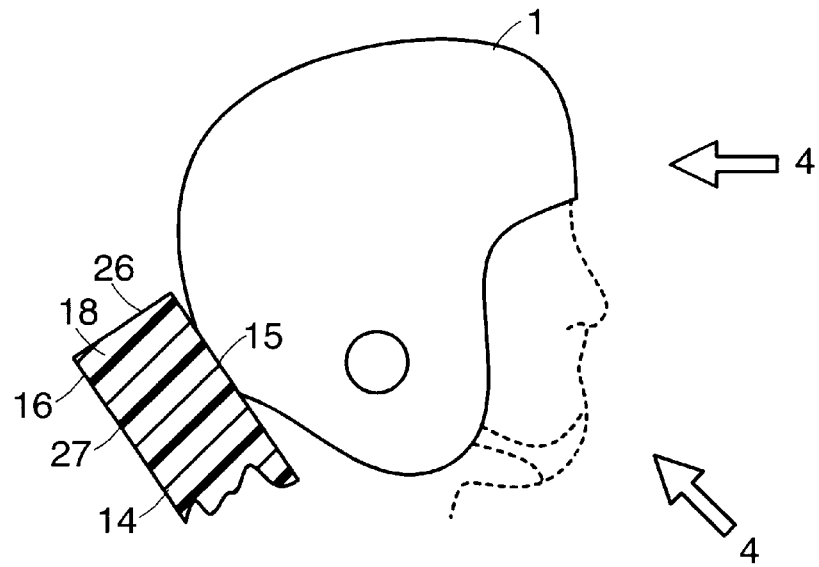
FIG. 8 is a side, fragmented diagrammic view of the neck brace reacting with a helmeted head under an extension-type force.
Figure 9:
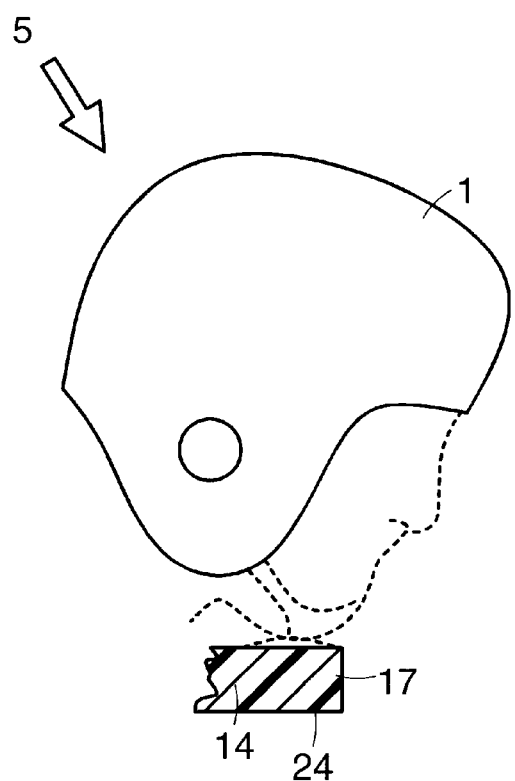
FIG. 9 is a side, fragmented diagrammic view of the neck brace reacting with a helmeted head under a flexion-type force.
Figure 10:
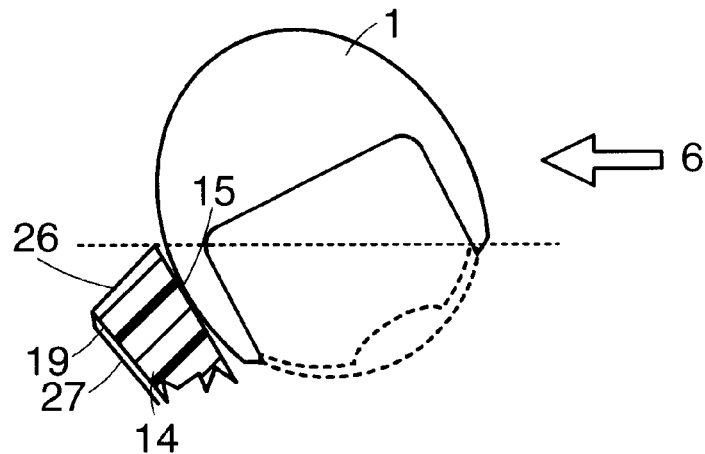
FIG. 10 is a front, fragmented diagrammic view of the neck brace reacting with a helmeted head under a lateral bending force.
Figure 11:
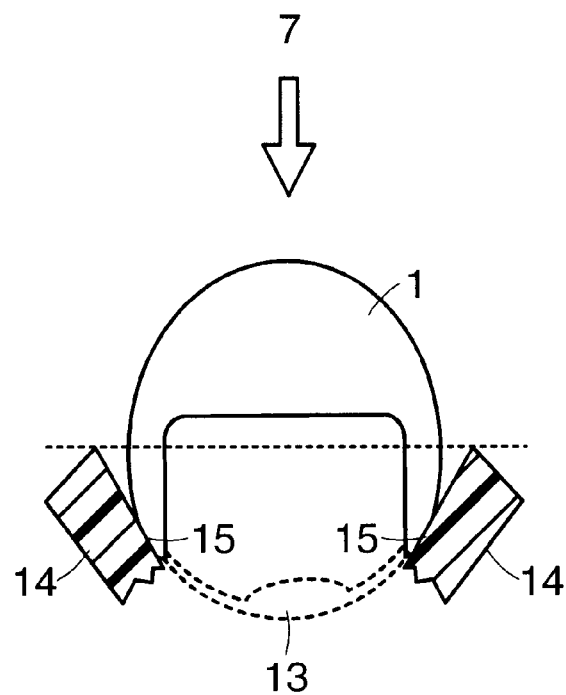
FIG. 11 is a front, fragmented diagrammic view of the neck brace reacting with a helmeted head under an axial-compression type force.

As may be seen most clearly from FIGS. 8 through 11, the brace 10 is adapted to providing protection to the helmeted head 1, and thereby the neck, regardless of the type of force being exerted. FIG. 8 illustrates the effect of the brace's rear 18 on extension forces 4 being exerted to the front of the helmeted head 1. The rear 18 of the brace wall 14 engages the helmeted head 1 as soon as frontal extension forces 4 are exerted, thereby countering the effect of the extension forces 4. FIG. 9 illustrates the effect of the brace's front 17 on flexion forces 5 being exerted to the rear of the helmeted head 1. The front 17 of the brace wall 14 engages the helmeted head 1 as soon as flexion forces 5 are exerted, thereby countering the effect of the flexion forces 5. The arrangement of fasteners 21, 25 and strap 23 holding the wall end portions 24, 24' in place provides sufficient cushioning at the brace front 17 to counter the flexion forces 5. FIG. 10 illustrates the effect of the brace's sides 19 on lateral bending forces 6 being exerted to the side of the helmeted head 1. The side 19 of the brace wall 14 engages the helmeted head 1 as soon as lateral bending forces 6 are exerted, thereby countering their effect. FIG. 11 illustrates the effect of the brace's wall 14 on axial compression forces 7 being exerted on the top the helmeted head 1. The inverted frustum-shaped central opening 13 literally funnels the helmeted head 1 into the cushioned interior surface 15 of the central opening 13 as soon as radial compression forces 7 are exerted, thereby countering their effect.

It is understood that the above-described embodiment is merely illustrative of the application. Other embodiments may be readily devised by those skilled in the art which will embody the principles of the invention and fall within the spirit and scope thereof. For example, the thickness of the brace 10 may be varied, as well as the central opening 13 size.

I claim:

1. A sports neck brace worn about a user's neck at a top neck opening of a user's shoulder pads, comprising:

a resilient brace member having a top, a bottom, a front, a rear, two sides and a wall extending from the bottom to the top and defining a generally inverted frustum-shaped central opening, said wall having an interior surface and exterior surface, said wall terminating in two wall ends at the brace front, said front having a vertical opening defined by said two wall ends;

a fastener attached to said wall end, each said wall end fastener adapted to engaging an opposite wall end fastener; and a strap fixedly attached to a first wall end front portion, said strap having a fastener attached to a strap inside surface;

a fastener fixedly attached to a second wall end front portion and being adapted to engaging the strap inside surface fastener.

2. A sports neck brace as recited in claim 1, wherein:

said wall exterior surface has an upper portion beginning at the brace member top and a lower portion terminating at the brace member bottom, said upper portion slanting downwardly and radially outwardly from the top of the central opening toward the brace member bottom and terminating in the lower portion, said lower portion slanting downwardly and radially inwardly from the upper portion toward the brace member bottom and terminating at the bottom of the central opening.

3. A sports neck brace as recited in claim 2, wherein:

said brace member bottom is contoured forming a radial ridge.

4. A sports neck brace as recited in claim 3, further comprising:

a wedge-shaped cut-out portion removably attached to the brace member bottom at the brace member rear.

5. A sports neck brace as recited in claim 4, wherein:

said brace member is made from foam covered by a smooth material.

\* \* \* \* \*